United States Patent [19]
Bartlett et al.

[11] Patent Number: 5,254,093
[45] Date of Patent: Oct. 19, 1993

[54] NON-REUSABLE HYPODERMIC SYRINGE
[75] Inventors: Joseph W. Bartlett, Lawndale; Gail F. Linn, Playa del Rey, both of Calif.
[73] Assignee: Medical Appliances, Inc., Los Angeles, Calif.
[21] Appl. No.: 478,667
[22] Filed: Feb. 12, 1990
[51] Int. Cl.$^5$ .............................................. A61M 5/00
[52] U.S. Cl. .................................. 604/110; 604/218
[58] Field of Search ............... 604/110, 111, 187, 199, 604/218, 221, 236–238, 240, 245, 220

[56] References Cited

U.S. PATENT DOCUMENTS

| 2,553,591 | 11/1946 | Poux . | |
|---|---|---|---|
| 4,233,975 | 11/1980 | Yerman . | |
| 4,391,272 | 7/1983 | Staempfli . | |
| 4,493,703 | 1/1985 | Butterfield . | |
| 4,687,467 | 8/1987 | Cygielski . | |
| 4,775,363 | 10/1988 | Sandsdalen . | |
| 4,775,364 | 10/1988 | Alles . | |
| 4,781,683 | 11/1988 | Wozniak et al. | 604/110 |
| 4,781,684 | 11/1988 | Trenner . | |
| 4,790,822 | 12/1988 | Haining . | |
| 4,804,370 | 2/1989 | Haber et al. | 604/110 |
| 4,820,272 | 4/1989 | Palmer . | |
| 4,826,984 | 5/1989 | Haber et al. | 604/110 |
| 4,827,547 | 5/1989 | Sahi et al. | 604/110 |
| 4,832,693 | 5/1989 | Gloyer . | |
| 4,850,968 | 7/1989 | Romano . | |
| 4,952,206 | 8/1990 | Ibanez et al. | 604/110 |

FOREIGN PATENT DOCUMENTS

| 2632190 | 12/1989 | France | 604/110 |
|---|---|---|---|
| 8903698 | 5/1989 | PCT Int'l Appl. | 604/110 |
| 8906146 | 7/1989 | PCT Int'l Appl. | 604/110 |
| 2205750 | 12/1982 | United Kingdom . | |

Primary Examiner—C. Fred Rosenbaum
Assistant Examiner—Mark Bockelman
Attorney, Agent, or Firm—Lyon & Lyon

[57] ABSTRACT

A single use disposable hypodermic syringe having a hollow elongated barrel portion, a piston and sealing engagement with an axially translatable along the barrel portion, a piston rod secured to the piston and projecting from the rearward end of the barrel portion for use in reciprocating the piston, a walled chamber disposed proximate the forward end of the barrel portion and plug means disposed in the chamber and moveable therein from a rearward position to a forward position in response to liquid being forced against the plug member by the piston. The plug member defines fluid passages therein to allow fluid flow about the plug member and an annular flange which cooperates with the interior surface of the chamber for maintaining the plug member in the rearward position upon air being passed through the fluid passages in response to translation of the piston within the barrel portion. The annular flange also cooperates with a second portion of the chamber wall for permanently maintaining the plug member in the forward position upon the plug member being moved to the forward position by the liquid during ejection thereon from the syringe. With the plug member in the forward position, the annular flange thereon seals the fluid passages upon the piston being retracted within the barrel portion toward the rearward end thereof to prevent any additional liquid from being aspirated into the barrel portion of the syringe about the plug member thereby rendering the syringe non-reusable.

38 Claims, 3 Drawing Sheets fig.1.

NON-REUSABLE HYPODERMIC SYRINGE

BACKGROUND OF THE INVENTION

The present invention relates to a non-reusable hypodermic syringe. As hypodermic syringes are used for inoculating against infectious diseases and administering prescribed medicines, the advantages of a non-reusable syringe are obvious. With the widespread use of illicit drugs and the spread of Acquired Immune Deficiency Syndrome, commonly known as AIDS, the present need for such a device is acute. While efforts have heretofore been made to provide such a device, as seen in U.S. Pat. Nos. 4,781,684, 4,832,693 and 4,850,968, such efforts have not met with widespread success as a result of deficiencies in the designs of the mechanisms developed to render syringes non-reusable.

A non-reusable syringe should not only be tamper-proof such that the means by which the device is rendered non-reusable can not be removed, but should also self-destruct without any cooperation of the user. For example, the syringe should not require a completion of the full stroke of the plunger within the barrel of the syringe to render the device inoperative as in the devices disclosed in the first two above-cited patents, or one could then leave the barrel of the syringe half full and continue to re-fill the upper part of the barrel. Second, it is important that a syringe be capable of acting as an air pump without rendering the syringe inoperative in order to maintain the interior of the vials of medicine at atmospheric pressure. When medicine is withdrawn from a standard vial of medicine by a hypodermic syringe, a negative pressure is created within the vial due to the air-tight seals used on such vials. Repeated withdrawal of medicine from the vial will build up a significant negative pressure within the vial. As the hypodermic needle on a syringe is withdrawn from a vial in which such a negative pressure has been created, air is aspirated into the syringe through the needle, creating small bubbles of air in the liquid medicine with the syringe which is extremely hazardous with intravenous injections. In addition, many injections require a combination of two medicines drawn from separate vials. If a negative pressure is allowed to build up within the vials, contamination and mixing problems will result as well as air bubbles. After drawing into the syringe the desired volume of medicine from the first vial and then inserting the syringe needle into a second vial which has a negative pressure therein, medicine will be drawn from the syringe back through the needle into the second vial, contaminating the medicine in the second vial and making an accurate measuring of the proportions of the two medicines in the syringe extremely difficult. To avoid these problems, it is common practice with conventional hypodermic syringes to first draw into the syringe a volume of air equal to the volume of medicine to be extracted from a particular vial and then inject that measured volume of air into the vial. Upon subsequently withdrawing an equal volume of medicine from that vial, the pressure within the vial will be left at atmospheric. In the single use hypodermic syringes heretofore developed, the means which render such devices non-reusable will act to render the syringe inoperative if one were to attempt to use it as an air pump in an effort to maintain the interior of the vial at atmospheric pressure. As a result, such devices are not only highly susceptible to the ingestion of air, but are also illsuited for injections requiring a mixture of medicines.

The non-reusable hypodermic syringe disclosed herein provides a single solution to all of the above problems by differentiating between the density of fluids therein and destructing solely in response to the ejection of liquid therefrom. The fluid density responsive destruct mechanism of the present invention will not activate upon the passage of air into and out of the syringe so that the syringe freely used as an air pump prior to any liquid being drawn therein to prevent negative pressure from building up in the vials of medicine. However, once a liquid has been drawn into the syringe and even a portion thereof ejected, the destruct mechanism is activated and no additional fluid, air or liquid, can be drawn into the syringe, rendering the device inoperable other than to eject the remaining liquid within the syringe.

SUMMARY OF THE INVENTION

The present invention provides a disposable and non-reusable hypodermic syringe. The syringe is rendered non-reusable by means of a fluid density responsive plug means disposed in a lower chamber of the syringe which, prior to aspirating liquid into the syringe, allows air to freely pass thereby so that the syringe can be used as an air pump to maintain atmospheric pressure within vials of medicine. Upon liquid being drawn into the syringe and a portion thereof ejected, the plug means is driven to an activated position by the hydraulic forces acting thereon, whereupon the plug means will allow the liquid to be ejected from the syringe but prevents any further refilling thereof.

In one embodiment of the invention, the fluid responsive plug means comprises a pair of axially aligned plug members disposed in the lower chamber of the syringe. The upper plug number is axially moveable within the chamber by means of the hydraulic forces acting thereon during liquid ejection from a raised inactive position to a lower active position. The upper plug member defines a fluid flow channel extending axially through the upper portion thereof, a conical recess extending rearwardly from the underside thereof which communicates with the fluid flow channel at its apex, and an annular resilient flange which projects outwardly from the plug member and bears against the chamber wall. The resilient flange cooperates with the surface of the chamber wall, first to retain the plug member in the raised inactive position both prior to use and while air is aspirated into and ejected from the syringe through the flow channel in the plug member so that the syringe can be used as an air pump, and second, to secure permanently the plug member in the lower active position upon a volume of liquid having been aspirated into the syringe and the plug member driven to said active position by the ejection of said liquid.

The lower plug member is disposed within the chamber below the upper plug member and is axially moveable therein in an area below the upper plug member. The lower plug member defines a conical extension on the upper end thereof which extends into the conical recess in the upper plug member such that upon the upper plug member being driven to the lowered active position, the lower plug member allows air or liquid to be ejected from the syringe but prevents return fluid channel fluid flow into the syringe. The lower plug member also defines fluid flow passageways in the side walls and the underside thereof to communicate the hypodermic needle carried by the forward end of the syringe with the area between the two plug members.

Prior to drawing fluid into the syringe through the hypodermic needle thereon, the upper plug member is held in the elevated position by the annular flange thereon bearing against the chamber wall. In this position, the piston disposed within the syringe above the upper plug member can be moved upwardly and downwardly to draw and expel air into and out of the syringe through the hypodermic needle. As the piston is moved downwardly within the syringe, air is forced through the fluid flow channel in the upper plug member into the conical recess in the lower portion thereof, about the lower plug member and is expelled through the hypodermic needle. Upward movement of the piston effects an opposite passage of air into the syringe.

Upon inserting the hypodermic needle into a vial of liquid medicine and raising the piston within the syringe, the liquid is drawn upwardly into the syringe about the lower plug member and through the upper plug member into the area within the syringe between the piston and the upper plug member. As the piston is pushed downwardly to eject the medicine, the hydraulic force of the liquid acting against the upper surface of the upper plug member causes the upper plug member to move downwardly, whereupon the annular flange thereon passes over a radially extending shoulder formed in the chamber wall into an enlarged diameter portion of the chamber and flexes outwardly. Concurrently, the liquid passes through the channel in the upper plug member into the recess in the underside thereof, about the lower plug member and into and out of the hypodermic needle. The force of the liquid flow passing through the upper plug member and against the lower plug member, maintains the lower plug member in lowered position within the chamber so that the conical extension thereon will not block the downward flow of any of the liquid through the upper plug member to the needle.

Upon the upper plug member having been moved downwardly such that the annular flange thereon passes into the enlarged diameter portion of the chamber, any subsequent retraction of the piston will not effect further aspiration of fluid into the syringe regardless of whether or not all of the liquid has been injected through the hypodermic needle. Such retraction of the piston will create a pressure drop in the syringe below the piston, causing the lower plug member to move rearwardly against the underside of the upper plug member which is prevented from moving rearwardly by the abutment of the annular flange thereon with the aforesaid shoulder in the chamber wall. When the lower plug member abuts the upper plug member the conical extension on the lower plug member will seal the lower end of the fluid flow channel extending through the upper plug member, rendering the syringe non-refillable and thus non-reusable.

In a second embodiment of the invention, a single plug member is disposed in a lower chamber of the syringe which is axially moveable therein by the hydraulic forces acting thereon during liquid ejection from a raised inactive position to a lower active position. The plug member defines a resilient flange which projects outwardly from the undersides thereof and cooperates with the interior wall surface of the chamber, first to retain the plug member in the raised inactive position both prior to use and while air is aspirated into and ejected from the syringe so that the syringe can be used as an air pump, and second, to retain the plug member in the lower active position upon a volume of liquid having been aspirated into the syringe and the plug member driven to said active position by the ejection of said liquid. In the raised inactive position air is free to pass through the lower syringe chamber and about the plug members therein by means of fluid flow passageways formed in the upper perimeter portion of the plug member and in the lower surface of the resilient flange. In the lower active position, any withdrawal of the piston in an effort to draw additional liquid into the syringe will draw the plug member rearwardly within the chamber causing a sealing engagement of the resilient flange with a shoulder formed in the chamber wall, preventing further aspiration of fluid into the syringe and thereby rendering the device non-reusable.

DESCRIPTION OF THE PREFERRED EMBODIMENTS

Figure 1:
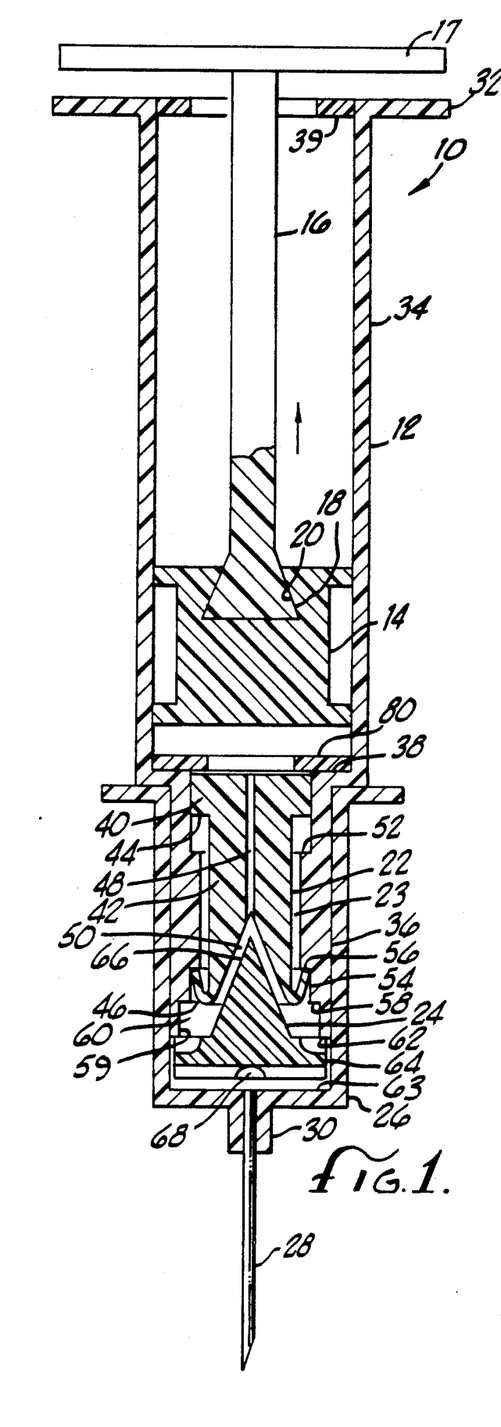
FIG. 1 is a sectional view of the hypodermic syringe of the present invention as fluid is being drawn therein.

The non-reusable hypodermic syringe 10 of the present invention includes a cylindrical barrel 12, a double-landed piston 14 and a plunger rod 16 for use in reciprocating the piston 14 within barrel 12. Rod 16 defines a gripping flange 17 on the rearward end thereof and is preferably secured to the piston 14 at its forward end by means of an enlarged tapered portion 18 held within a correspondingly configured recess 20 in the rearward portion of piston 14. An upper plug member 22 is disposed below piston 14 within a chamber 23 defined by the lower portion of barrel 12 and a barrel cap 26. A lower plug member 24 is disposed in chamber 23 axially below plug member 22. Barrel cap 26 is permanently affixed to the lower end of barrel 12 by heat bonding on a suitable adhesive, and a hypodermic needle 28 is permanently secured within a hollow extension 30 extending from barrel cap 26.

The syringe barrel 12, which is preferably constructed of a transparent durable plastic material, defines an outwardly extending radial flange 32 at the upper end thereof, a constant diameter upper portion 34 within which piston 14 is axially translatable, a lower portion 36 which defines the interior wall of chamber 23 and an intermediary annular horizontal end wall 38. A stop ring 39 is provided at the rearwardmost end of barrel 12 to prevent withdrawal of the piston from the barrel so as to preclude access to the interior of the barrel.

The upper plug member 22, preferably constructed of a rubber material includes an enlarged diameter upper portion 40, a body portion 42, a shoulder 44 disposed therebetween, a resilient annular flange 46 extending outwardly from the lower end thereof, and a fluid channel 48 extending axially therethrough and communicating with a conical recess 50.

Shoulder 44 is adapted to abut a first shoulder 52 defined by the lower portion 36 of barrel 12 in chamber 23 to limit the downward movement of the upper plug member 22 within chamber 23. As seen in FIG. 1, the resilient annular flange 46 extends outwardly and upwardly from the lower end of plug member 22 such that when the upper plug member 22 is in the raised inactive position, flange 46 flexes outwardly and bears against side wall 54 in chamber 23 and abuts a second shoulder 56 defined by the lower portion 36 of barrel 12 in chamber 23 to limit the upward travel of plug member 22 within chamber 23. The lower portion 36 of syringe barrel 12 also defines a third interior shoulder 58 in chamber 23 located between side wall 54 and a lower side wall 59 disposed about an enlarged diameter portion 60 of chamber 23 adjacent the lower end 62 of barrel 12.

Figure 5:
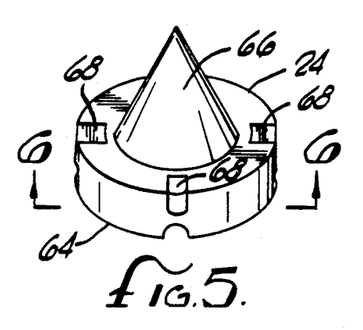
FIG. 5 is prospective view of the lower plug members of the present invention.
Figure 6:
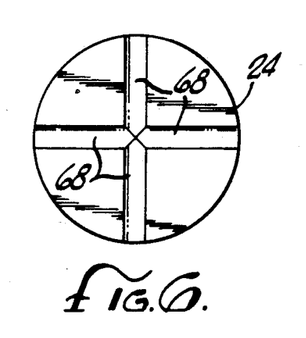
FIG. 6 is a view taken along line 6—6 in FIG. 5.

The lower plug member 24, also preferably constructed of a rubber material, is disposed axially below upper plug member 22 in chamber 23. Lower plug member 24 defines a lower base portion 64, and a conical extension 66. Lower base portion 64 defines a diameter less than the inner diameter of end cap 26 to allow fluid flow therebetween but greater than the inner diameter of barrel 12 at the end 62 thereof so as to be axially translatable within chamber 23 between the lower end wall 63 of barrel cup 26 and the lower end 62 of barrel 12. Extension 66 projects upwardly from base portion 64 into the recess 50 in the upper plug member 22, and is configured so as to abut and mate with the conical side wall of recess 50 upon the plug members being forced together so as to seal the lower end of fluid channel 48 in the upper plug member 22 to prevent fluid flow therethrough. As seen in FIG. 5 and 6, fluid passages 68 are formed in the side and bottom walls of the lower plug member 24 so as to communicate the hypodermic needle 28 with the portion of chamber 23 above the lower plug member 24 so as to allow fluid flow therebetween about lower plug member 24 when the lower plug member is in its lowermost position against end wall 63 of barrel cap 26.

Prior to any fluid being drawn into the syringe 10 through needle 28, the upper plug member is in the raised position in chamber 23 as illustrated in FIG. 1. In this position, the syringe 10 can be used as an air pump by means of piston 14, as the downward movement of piston 14 will force air in barrel 12 through chamber 23 via the channel 48 in the upper plug member 22, about the lower plug member 24 and out needle 28, but will not create sufficient force against the upper end of plug member 22 to move the plug member downwardly within chamber 23. Accordingly, if one needed an injection of, for example, 20 units of medicine, the user would retract the piston to a point slightly above the 20 unit mark on the barrel (not shown), insert the needle into the liquid medicine in the vial through the standard seal thereon, push the piston back down to wall 38 to drive a volume of air slightly in excess of 20 units into the vial and retract the piston to the point slightly above the 20 unit mark to draw slightly over 20 units of medicine into the barrel of the syringe. The syringe is then held in an inverted position with the needle pointing upwardly, and the piston is again pushed back to the 20 unit mark, ejecting the excess medicine from the needle as well as any air remaining in the syringe. The syringe is then ready to inject the measured 20 units of medicine into the user and, due to the air pumping capability of the syringe, the interior of the vial of medicine is left at atmospheric pressure.

Figure 2:
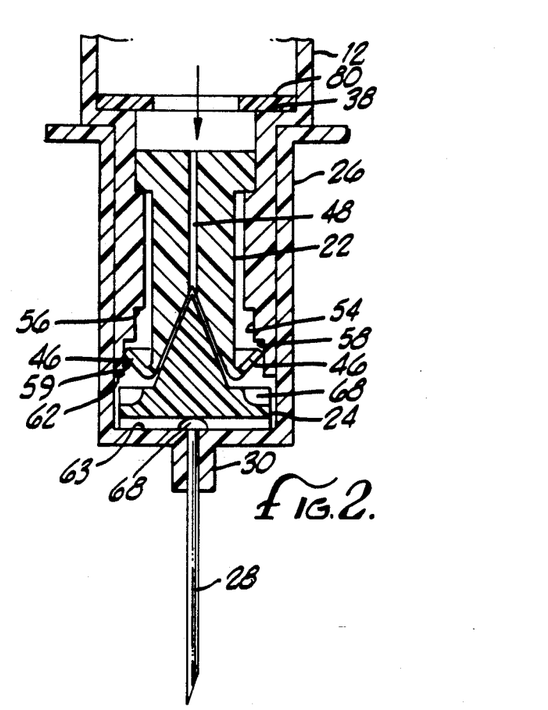
FIG. 2 is a sectional view of the lower portion of the hypodermic syringe of the present invention showing the relative positioning of the plug members as liquid is being ejected from the syringe.
Figure 3:
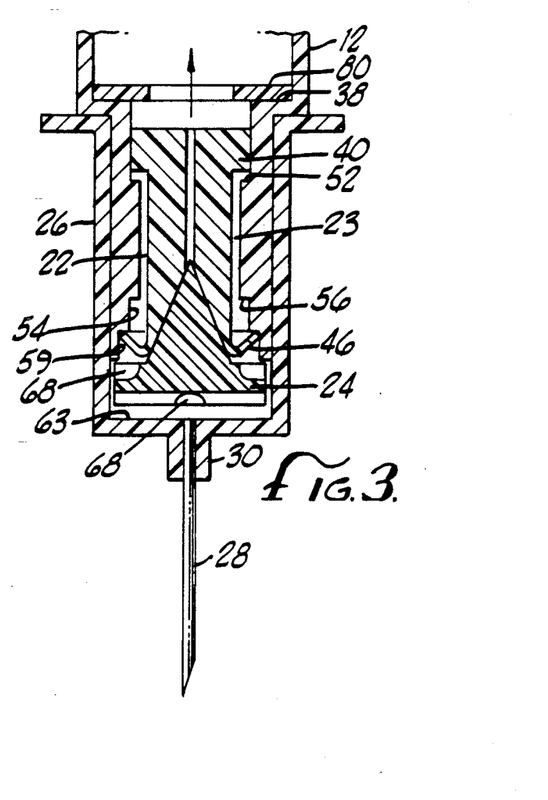
FIG. 3 is a partial sectional view of the lower portion of the hypodermic syringe of the present invention during an attempted refilling of the syringe.

As the piston 14 is then driven downwardly during the injection, the liquid medicine is forced through the channel 48 in the upper plug member 22, about the lower plug member 24 through the fluid passages 68 therein and into and out of the hypodermic needle 28. Concurrently, the hydraulic forces created during the injection by the liquid being driven by the piston act on the effective upper surface areas of the upper and lower plug members 22 and 24 to drive the upper plug member 22 downwardly within chamber 23 to the position illustrated in FIG. 2 and the lower plug member 24 downwardly against the lower end wall 63 of cap member 26. As the resilient flange 46 on the upper plug member 22 passes the shoulder 58 in chamber 23, the flange flexes outwardly within the enlarged diameter portion 60 of chamber 23 and bears against the side wall 59 of the enlarged diameter portion 60 of chamber 23. The upper and lower plug members will then remain in this position during the injection. If, either after the completion of the injection or during the injection, one were to attempt to retract the piston 14 within the barrel to aspirate more liquid into the syringe through needle 28, the resultant vacuum created within the barrel below the piston 14 would draw the upper and lower plug members upwardly to the positions illustrated in FIG. 3. The upward travel of upper plug member 22 during such an attempted refill would be limited by the abutment of the flange 46 thereon with shoulder 58 in chamber 23, while the conical extension 66 on the lower plug member 24 would be drawn into recess 50 and against the upper plug member, sealing the lower end of channel 48, and thereby preventing any fluid flow upwardly through the upper plug member 22. The sealing engagement of flange 46 with the side wall 59 and shoulder 58 in chamber 23 would prevent any upward fluid flow about the upper plug member 22. Accordingly, prior to drawing any liquid into the syringe 10, the piston can be moved upwardly and downwardly within the barrel without effecting deactivation of the syringe. However, once a liquid has been drawn into the syringe and the piston moved downwardly a slight distance sufficient to cause a translation of the lower plug member 22 a distance equal to axial length of side wall 54, flange 46 clears shoulder 58, flexes outwardly and the syringe is rendered inoperative, other than to eject the fluid contained therein without any affirmative action or other cooperation of the user.

While the above mechanism provides a non-reusable syringe which cannot be refilled by the user, to dissuade one from continuing to try to make the device function properly or from even attempting to disassemble the syringe to remove the disabling plug members, the enlarged tapered end 18 of the plunger rod 16 by which the rod is secured to piston 14 is configured to separate from the piston in the event one were to attempt to draw additional fluid into the syringe. Once the upper plug member has been driven forwardly to the lower position by injection of liquid from the syringe, any subsequent retraction of the piston within the barrel will create a vacuum within the barrel between the piston and upper plug member as a result of the sealing engagements of the upper and lower plug members 22 and 24. As this vacuum increases with the retraction of the piston, the opposed forces acting on the upper and lower ends of the piston will cause the enlarged tapered end 18 of the plunger rod 16 to be pulled out of the tapered recessed 20 in the piston, separating the rod 18 from piston 14 and making the destruction of the syringe readily apparent to the user so as to dissuade the user from any further attempts to use the device or to try to disassemble and reconstruct the syringe. In addition, a washer 80 could be provided on barrel wall 38 which extends slightly over the upper perimeter surface of upper plug member 22 to prevent one from being able to somehow pull the plug members from the barrel. Alternatively, end wall 38 could be extended radially inwardly to provide the same function.

Figure 4:
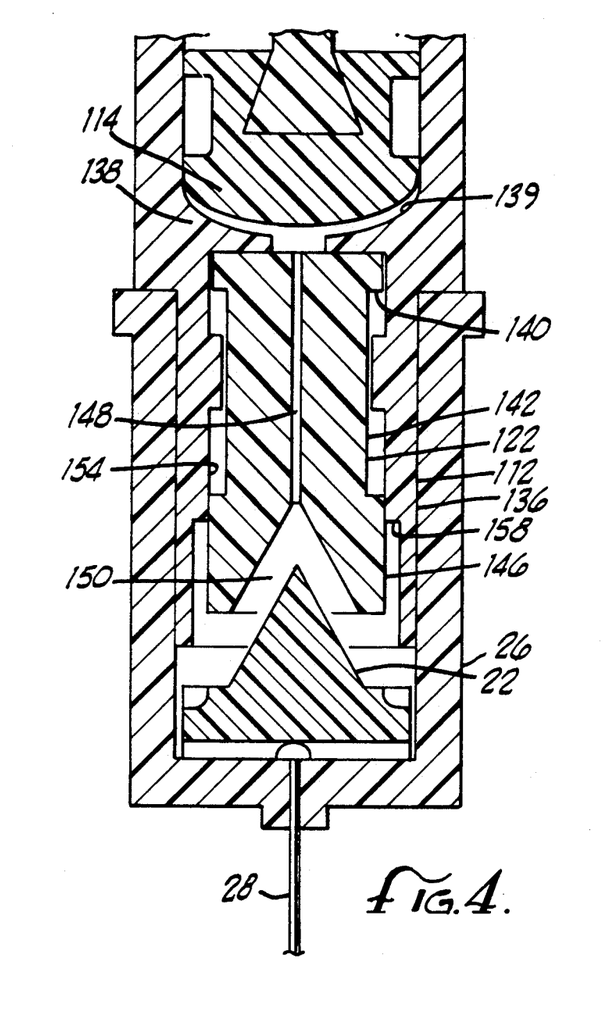
FIG. 4 is a partial sectional view of lower portion of a modified form of the present invention.

FIG. 4 illustrates a modified form of the above described embodiment of the invention which, while operating in the same manner as the prior embodiment, differs slightly from the prior embodiment in the configuration of the upper plug member 122 and the lower portion 136 of the syringe barrel 112. In the second embodiment, the upper plug member 122 which, like the upper plug member 22 of the prior embodiment, is preferably constructed of a resilient rubber material, comprises an enlarged diameter upper radial flange portion 140, a central body portion 142 of reduced diameter, an enlarged lower radial flange portion 146, a central axial fluid channel 148, and conical recess 150. The enlarged lower flange portion 146 is sized so as to be in slight compression against a side wall 154 defined by barrel 112 to retain plug member 122 in place prior to ejection of liquid therethrough and such that upon plug member 122 being forced downwardly by the hydraulic forces acting thereon during liquid ejection, the enlarged lower flange portion 146 will flex outwardly upon clearing a shoulder 158 defined in the lower portion of the barrel to maintain the plug member 122 in a lowered position and, in combination with a lower plug number 24, disable the syringe from being able to draw additional liquid therein in the same manner as described above with respect to the prior embodiment.

In addition, the syringe barrel can be modified as seen in FIG. 4 to provide an inwardly extending radial flange 138 having an upper curvalinear surface 139. Flange 138 prevents withdrawal of the plug members from the barrel, while the upper curvalinear surface 139 thereon will assist the user in aligning any air bubbles in the medicine with the fluid flow channel 148 in the upper plug member 122 for removal through needle 28. The configuration of flange 138 can be used with either embodiment of the invention. However, when using flange 138, the lower surface of the piston should be corresponding configured as seen at 114 in FIG. 4.

FIGS. 7-10 illustrate a second embodiment of the invention which employs only a single plug member to render the syringe non-reusable. The syringe 200 of the second embodiment differs from syringe 10 solely in the lower portion thereof and accordingly only the lower portion of syringe 200 will be described. Syringe 200 includes a barrel 202 defining a constant diameter portion 204 within which a piston 206 is disposed. Piston 206 is preferably provided with a curvalinear lower surface 208 and is carried by plunger rod 210. Barrel 202 defines a lower syringe chamber 211, an annular shoulder 212 disposed in chamber 211 and a curvalinear lower surface 214 having a concave position 216 terminating a flat horizontal surface 218 having a central opening 220 therein. A barrel cap 222 is carried by the lower end of barrel 202 and a hypodermic needle 223 is carried by barrel cap 222 such that it communicates with chamber 211 through the opening 220 in barrel cap 222.

Figures 7, 8, 9, 10:
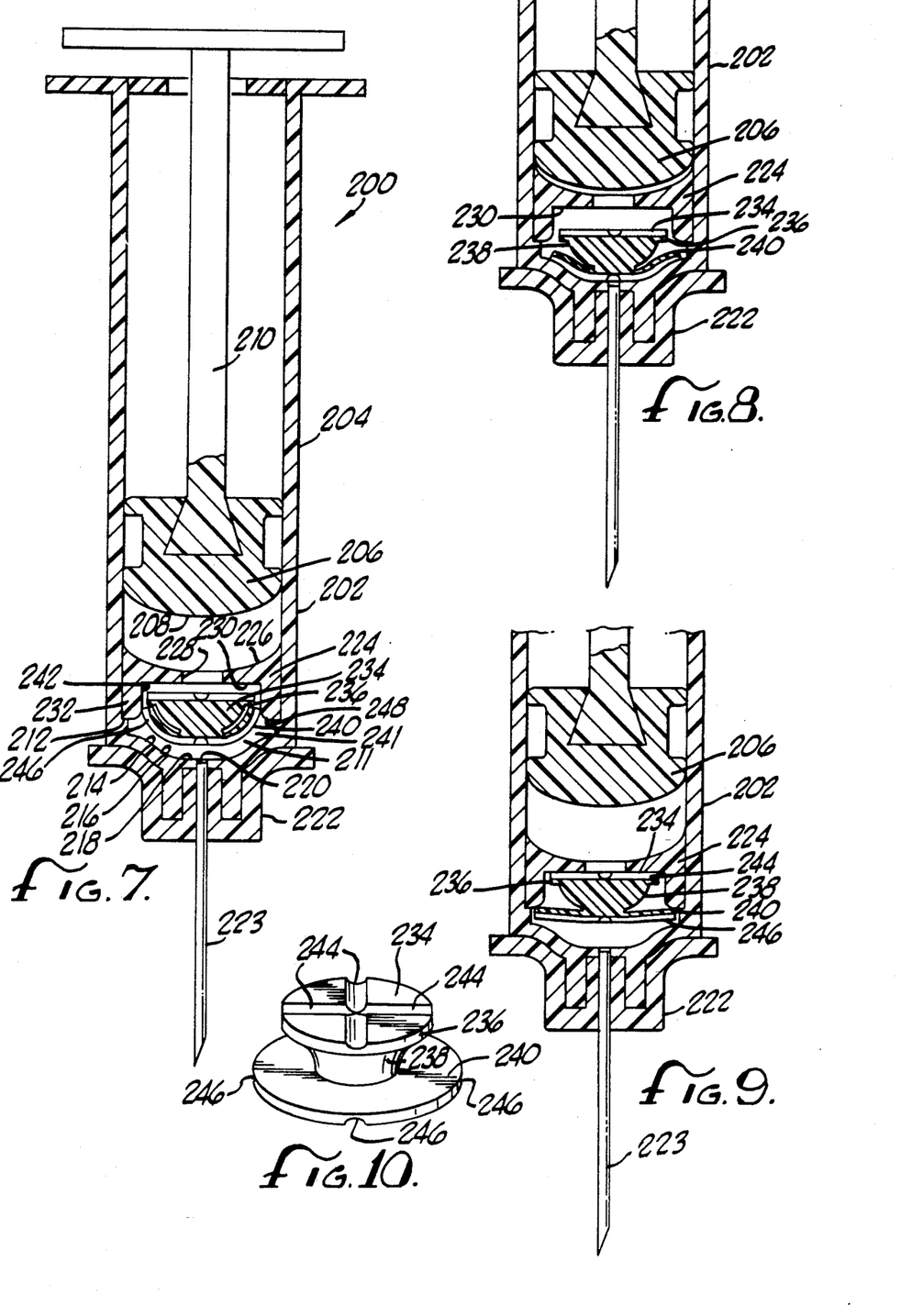
FIG. 7 is a sectional view of a second embodiment of the present invention showing the position of the plug member prior to liquid been drawn therein.
FIG. 8 is a partial sectional view of the lower portion of a second embodiment of the present invention showing the position of the plug member as liquid is being ejected from the syringe.
FIG. 9 is a partial sectional view of the lower portion of a second embodiment of the present invention showing the position of the plug member during an attempted refilling of the syringe.
FIG. 10 is a perspective view of the plug member of the second embodiment of the invention.

An annular stop member 224, preferably constructed of the same durable plastic material as barrel 202, is affixed to the interior surface of barrel 202 so as to define the upper end of chamber 211. Stop member 224 defines a curvalinear upper surface 226 adapted to mate with the correspondingly configured lower surface 208 of piston 206, a central opening 228 therein, a flat horizontal lower surface 230 and an annular depending portion 232 which abuts shoulder 212 in chamber 211.

A plug member, preferably 234 constructed of a rubber material, is disposed within chamber 211, and defines: an upper portion 236, a curved downwardly tapered portion 238 which is disposed below portion 236 and inwardly spaced from the perimeter thereof, and a resilient lower annular flange 240 disposed below tapered portion 238. The outer diameter of the upper portion 236 of plug member 234 is less than the inner diameter defined by the interior side wall 242 of stop member 224 so as to allow fluid flow therebetween. For reasons which will become readily apparent, the diameter of lower flange 240 in the unflexed state, as seen in FIG. 9, is greater than the inner diameter defined by interior side wall 242. As seen in FIG. 9, fluid passageways 244 and 246 are provided in the upper surface of plug member 234 and in the underside of resilient flange 240 respectively to allow for fluid flow about the plug member. Alternatively, the fluid passageways could be formed in the lower surface 230 and depending portion 232 of stop member 224 and in the lower surface 214 of barrel 202 to allow for such flow.

In the raised inactive position illustrated in FIG. 7, flange 240 is disposed substantially adjacent the tapered portion 238 of the plug member 234, flexes outwardly and bears against the side wall 242 so as to retain the plug member 234 in the raised inactive position. Prior to any liquid being drawn into the syringe 200, the syringe can be used as an air pump, as with the prior embodiment, as air is free to pass through chamber 211 about plug member 234 via fluid passageways 244 and 246 without moving the plug member. Upon a liquid being drawn into the syringe and the piston 206 being moved downwardly, the liquid is forced through chamber 211, about plug member 234 through the fluid passageways 244 and 246 therein and out needle 224. Concurrently, the hydraulic forces acting on plug member 234, force the plug member downwardly within chamber 211, causing flange 240 to move past the lower end 248 of stop member 224 and against the lower surface 214 of the barrel 202 to the position illustrated in FIG. 8. As soon as flange 240 clears end 248, it flexes outwardly in the enlarged diameter portion 241 of chamber 211 and the plug member 234 is in the active position. Thereafter, withdrawal of the piston 206 in an effort to draw more liquid into the syringe will cause the plug member to be drawn rearwardly within chamber 211 such that the upper surface 249 of flange 240 will abut the lower end 248 of stop member 224 and prevent fluid passage therebetween as seen in FIG. 9, thereby rendering the syringe non-reusable.

The sensitivity of the embodiments of the non-reusable syringe of the present invention is determined by the axial distance the flange 46 on the first embodiment, the enlarged flange portion 146 on the modified form thereof, or the flange 240 on the second embodiment, travels before flexing outwardly to secure the plug member in its lower active position. For example, in the second embodiment this distance depends on the axial length of the depending portion 232 of stop member 224. By increasing this axial length, or the length of side wall 54 in the first embodiment, the syringe could be designed to allow for ejection of a small amount of liquid prior to the plug member being locked in its lower active position. This would provide the user with some flexibility in the event of inadvertly ejecting slightly too much liquid during air expulsion prior to an injection as the user could then draw a portion of an additional unit of medicine into the syringe to correct the error.

Various other changes and modifications may be made in carrying out the present invention without departing from the spirit and scope thereof. Insofar as these changes and modifications are within the purview of the appended claims, they are to be considered as part of the present invention.

We claim:

1. A single use disposable hypodermic syringe comprising:
   a hollow elongated barrel portion;
   a piston in sealing engagement with and axially translated along said barrel portion;
   a piston rod secured to said piston and projecting from one end of said barrel portion for use in reciprocating said piston;
   a walled chamber disposed proximate the other end of said barrel portion;
   a first plug member disposed in said chamber and moveable therein from a rearward position to a forward position;
   a second plug member disposed forwardly of said first plug member;
   fluid flow means disposed in said first plug member for allowing fluid flow therethrough;
   means defined by said first plug member for maintaining said first plug member in said rearward position upon air being drawn into and ejected from said barrel portion through said fluid flow means in response to translation of said piston within said barrel portion and for permanently maintaining said first plug member in said forward position upon said first plug member being moved to said forward position by said liquid during ejection thereof from said syringe; and
   means defined by said second plug member for sealing said fluid flow means upon said first plug member being forced to said forward position and said piston being retracted within said barrel portion toward said one end thereof to prevent any additional liquid from being drawn into said barrel portion through said fluid flow means thereby rendering said syringe non-reusable.

2. A single use disposable hypodermic syringe comprising:
   a hollow elongated constant diameter barrel portion;
   a piston in sealing engagement with and axially translatable along said barrel portion;
   a piston rod secured to said piston and projecting from one end of said barrel portion for use in reciprocating said piston;
   a walled chamber disposed proximate the other end of said barrel portion;
   a first plug member disposed in said chamber and defining means therein to allow fluid flow therethrough, said plug member being moveable from a rearward position to a forward position in response to liquid being forced against said plug member by said piston;
   a second plug member disposed in said chamber forwardly of said first plug member and defining means for allowing liquid flow about said second plug member for ejection from said syringe and means for sealing said fluid flow means in said first plug member upon said second plug member being forced against said first plug member when said first member is in said forward position; and
   means for maintaining said first plug member in said rearward position upon air being passed therethrough in response to translation of said piston within said barrel portion and for permanently maintaining said plug member in said forward position upon said first plug member being moved to said forward position by said liquid during ejection thereof from said syringe such that upon said first plug member being forced to said forward position and said piston being retracted within said barrel portion toward said one end thereof, said second plug member is caused to be drawn rearwardly within said chamber against said first plug member, sealing said fluid flow means therein and preventing any additional liquid from being aspirated into said barrel through said first plug member thereby rendering said syringe non-reusable.

3. The syringe of claim 2 wherein said maintaining means comprises an annular resilient flange projecting from said first plug member against a portion of the wall of said chamber and a radial shoulder defined by said wall such that upon said first plug member being forced from said rearward position to said forward position, said flange passes forwardly of said shoulder and flexes radially outwardly therefrom, and upon said piston being subsequently retracted within said barrel portion, abuts said shoulder to maintain said first plug member in said forward position.

4. The syringe of claim 3 wherein said fluid flow means in said first plug member comprises a fluid flow channel extending axially therein and communicating with a conical recess formed in said first plug member and wherein said sealing means on said second plug member comprises a conical extension thereon adapted to be received within said recess in said first plug member and seal said fluid flow channel therein.

5. The syringe of claims 2, 3 or 4 including a cap member disposed about the forward end of said walled chamber, said cap member defining a central opening in the forward end thereof and wherein said second plug member is axially moveable within said chamber between the forward end of said cap member and the forward end of said chamber wall.

6. The syringe of claim 5 wherein said piston rod defines an enlarged portion at the forward end thereof, said portion being received and held within a correspondingly configured recess in said piston such that upon said first plug member being disposed in the forward position and said piston being retracted within said barrel portion, a vacuum is created between said piston and said first plug member causing said enlarged portion of said piston rod to be pulled from said recess, rendering said piston rod incapable of further reciprocation of said piston.

7. A single use disposable hypodermic syringe comprising:
- a hollow elongated barrel having a forward end and a rearward end;
- a piston in sealing engagement with and axially translatable along a first portion of said barrel;
- a piston rod secured to said piston and projecting from the rearward end of said barrel for use in reciprocating said piston;
- a first plug member disposed in a second portion of said barrel forwardly of said piston, said member being moveable from a rearward position to a forward position within said second barrel portion in response to liquid being forced against said member by said piston and defining a fluid flow channel extending axially therethrough;
- a second plug member disposed in said barrel forwardly of said first plug member and defining one or more channels therein for the passage of fluid about said second plug member and means thereon for sealing said fluid flow channel in said first plug member upon said plug members being disposed in an abutting relationship to prevent fluid flow through said channel; and
- means for maintaining said first plug member in said rearward position and spaced from said second plug member to allow a variable volume of air to be drawn into and ejected from said barrel through said channel in said first plug member and about said second plug member in response to reciprocation of said piston within said barrel prior to liquid being drawn into said barrel whereby said syringe can operate as an air pump and, upon liquid being drawn into said barrel about said second plug member and through said channel in said first plug member and said first plug member being forced forwardly within said barrel to said forward position during ejection of liquid from said barrel by the force of the liquid acting on said first plug member, said means maintains said first plug member in said forward position such that upon said piston being retracted toward said rearward end of said barrel, said second plug member is caused to be drawn rearwardly against said first plug member, sealing said fluid flow channel in said first plug member and preventing any additional fluid from being drawn into said barrel through said first plug member thereby rendering said syringe non-reusable.

8. The syringe of claim 7 wherein said maintaining means comprises an annular resilient flange formed with and projecting outwardly from said first plug member and bearing against a first portion of said barrel when said first plug member is disposed in said rearward position to maintain said plug member in said rearward position prior to the ejection of liquid from said barrel, and a stop member in said barrel disposed forwardly of and radially outwardly from said first portion of said barrel such that upon said first plug member being forced to said forward position by said liquid during ejection thereof, said flange passes forwardly of said stop member, flexes outwardly and bears against a second portion of said barrel disposed below said stop member whereby said first plug member is permanently held in said forward position by the abutment of said flange with said stop member.

9. The syringe of claims 7 or 8 wherein said first plug member includes a conical chamber formed therein communicating with said fluid flow channel and wherein said sealing means defined by said second plug member comprises a conical extension thereon adapted to be received within said chamber in said first plug member and seal said fluid flow channel therein.

10. The syringe of claim 9 including a cap member disposed about the forward end of said barrel and defining a central opening in the forward end thereof, said second plug member being axially moveable between the forward end of said cap member and the forward end of said barrel.

11. The syringe of claims 7 or 8 wherein said piston rod defines an enlarged portion at the forward end thereof, said portion being received and held within a correspondingly configured recess in said piston such that upon said first plug member being disposed in said forward position and said piston being retracted in said barrel, a vacuum is created between said piston and said first plug member such that upon retracting said piston within said barrel, said enlarged portion of said piston rod is caused to be pulled from said recess, rendering said piston rod incapable of further reciprocation of said piston.

12. A single use hypodermic syringe comprising:
- a hollow elongated barrel having a forward end, a rearward end, and a constant diameter portion adjacent said rearward end;
- a piston in sealing engagement with and axially translatable along said constant diameter portion of said barrel;
- a piston rod secured to said piston and projecting from said rearward end of said barrel for use in reciprocating said piston;
- a first plug member disposed in said barrel forwardly of said piston and defining a fluid flow channel extending axially therethrough and means cooperating with said barrel for retaining said plug member within a first portion of said barrel as a variable volume of air is drawn into and ejected from said barrel in response to translation of said piston within said barrel prior to liquid being drawn into said barrel whereby said syringe can operate as an air pump, said means, retaining said plug member within a second portion of said barrel upon liquid having been drawn into said barrel and ejected therefrom through said channel so as to move the plug from first to second portion of the barrel; and
- a second plug member spaced from said first plug member, said second plug member having flow passages therein for the passage of fluid about said second plug member and means thereon for sealing said channel in said first plug member upon said first plug member being disposed within said second portion of said barrel and said piston being retracted toward said rearward end thereof whereby liquid is prevented from being further drawn into said barrel through said first plug member, rendering said syringe non-reusable.

13. The syringe of claim 12 wherein said piston rod defines an enlarged portion at the forward end thereof, said portion being received and held within a correspondingly configured recess in said piston such that upon said first plug member being disposed in said second portion of said barrel and said piston being retracted within said barrel, a vacuum is created between said piston and said first plug member such that upon retracting said piston within said barrel, said enlarged portion of said piston rod is caused to be pulled from said recess, rendering said piston rod incapable of further reciprocation of said piston.

14. The syringe of claims 12 or 13 wherein said barrel defines a first stop member and a second stop member, said second stop member being disposed forwardly of and spaced radially outwardly from said first stop member and wherein said cooperating means comprises an annular resilient flange formed with and projecting outwardly from said first plug member and bearing against a portion of said barrel below said first stop member when said first plug member is disposed in said first portion of said barrel thereby restricting the rearward movement of said first plug member in said barrel and maintaining said first plug member in place as air is drawn into and ejected from said barrel and, upon said first plug member being forced to said second portion by said liquid during ejection thereof, said flange passes forwardly of said second stop member, flexes outwardly and bears against a portion of the barrel disposed below said second stop member whereby said first plug member is permanently held within said second portion of said barrel by the abutment of said flange with said second stop member.

15. A single use disposable hypodermic syringe comprising:
    a hollow elongated barrel having a forward end, a rearward end and a constant diameter portion adjacent said rearward end;
    a piston in sealing engagement with and axially translatable along said constant diameter portion of said barrel;
    a piston rod secured to said piston and projecting from said rearward end of said barrel for use in reciprocating said piston;
    a cap member secured to and disposed about said forward end of said barrel and defining a central opening therein;
    a cannula means carried by said cap member and communicating with said central opening;
    a first plug member disposed in said barrel forwardly of said piston and defining a fluid flow channel extending axially therethrough, a first stop means adapted to abut a first shoulder defined by said barrel to limit the forward movement of said plug member within said barrel, and an annular resilient flange member in sealing engagement with said barrel to prevent fluid flow therebetween and retain said plug member within a first portion of said barrel as a variable volume of air is drawn into and out of said barrel through said cannula means prior to liquid being drawn into said barrel whereby said syringe can operate as an air pump and, upon said plug member being forced forwardly of said first portion of said barrel during the ejection of liquid from said barrel by the force of the liquid acting on said plug member, to cooperate with a second shoulder defined by said barrel to retain said plug member within a second forward portion of said barrel; and
    a second plug member disposed forwardly of said first plug member and defining means thereon for sealing said fluid channel in said first plug member upon said first plug member being disposed in said second forward portion of said barrel and said piston being retracted toward said rearward end of said barrel, whereby any additional liquid is prevented from being drawn into said barrel through said flow channel in said first plug member thereby rendering said syringe non-reusable.

16. The syringe of claim 15 wherein said piston rod defines an enlarged portion at the forward end thereof, said portion being received and held within a correspondingly configured recess in said piston such that upon said first plug member being disposed in said second portion of said barrel and said piston being retracted within said barrel, a vacuum is created between said piston and said first plug member such that upon retracting said piston within aid barrel, said enlarged portion of said piston rod is caused to be pulled from said recess, rendering said piston rod incapable of further reciprocation of said piston.

17. The syringe of claims 15 or 16 wherein said first plug member defines a conical chamber therein communicating with said fluid channel and wherein said sealing means defined by said second plug member comprises a conical extension thereon adapted to be received within said chamber in said first plug member and seal said flow channel therein.

18. A single use disposable hypodermic syringe comprising:
    a hollow elongated barrel portion;
    a piston in sealing engagement with and axially translatable along said barrel portion;
    a piston rod secured to said piston and projecting from one end of said barrel portion for use in reciprocating said piston;
    a walled chamber disposed proximate the other end of said barrel portion; and
    axially translatable plug means constructed of a liquid impervious material disposed in said chamber and movable therein from a rearward position to a forward position, said plug means defining fluid flow means therein, said fluid flow means being continuously open when said plug means is in said rearward position and, prior to liquid being drawn into said barrel portion, a allowing a variable volume of air to pass therethrough and be drawn into and ejected from said barrel portion in response to translation of said piston within said barrel portion during the use of the syringe as an air pump and, upon liquid being drawn into said barrel portion through said fluid flow means and least a portion thereof ejected from said syringe, said plug means sealing said fluid flow means in response to said piston being retracted within said barrel portion toward said one end thereof and preventing any additional liquid from being aspirated into said barrel portion through said fluid flow means thereby rendering said syringe non-reusable.

19. The syringe of claim 18 wherein said piston rod defines an enlarged portion at the forward end thereof, said portion being received and held within a correspondingly configured recess in said piston such that upon said plug member being disposed in said forward position and said piston being retracted in said barrel, a vacuum is created between said piston and said first plug member such that upon retracting said piston within said barrel, said enlarged portion of said piston rod is caused to be pulled from said recess, rendering said piston rod incapable of further reciprocation of said piston.

20. A single use disposable hypodermic syringe comprising:
a hollow elongated barrel;
a piston in sealing engagement with and axially translatable along said barrel portion;
a piston rod secured to said piston and projecting from one end of said barrel portion for use in reciprocating said piston;
a first plug member disposed in a portion of said barrel forwardly of said piston and moveable from a rearward position to a forward position in response to liquid being forced against said plug member by said piston, said plug member defining a fluid flow channel therein for allowing a variable volume of air to pass therethrough and be drawn into and ejected from said barrel in response to translation of said piston within said barrel prior to liquid being drawn into said barrel whereby said syringe can operate as an air pump;
means for permanently maintaining said first plug member in said forward position upon said plug member being moved to said forward position; and
a second plug member movably disposed in said barrel forwardly of said first plug member, said second plug member defining closure means thereon for sealing said fluid flow channel upon said first plug member being disposed in said forward position and said closure means being drawn into sealing engagement with said channel upon the retraction of said piston within said barrel.

21. A single use disposable hypodermic syringe comprising:
a hollow elongated barrel portion;
a piston in sealing engagement with and axially translatable along said barrel portion;
a piston rod secured to said piston and projecting from one end of said barrel portion for use in reciprocating said piston;
a walled chamber disposed proximate the other end of said barrel portion;
a plug member disposed in said chamber and movable therein from a rearward position to a forward position in response to liquid being forced against said plug member by said piston, said plug member having a fluid flow channel therein allowing for the passage of fluid therethrough to and from said barrel portion when said plug member is in said rearward position;
resilient retaining means carried by said plug member for retaining plug member in said rearward position prior to liquid being drawn into said barrel portion and allowing a variable volume of air to be drawing into and ejected from said barrel portion through said channel when said piston is reciprocated within said barrel portion during the use of said syringe as an air pump; and
means disposed in said chamber for closing said fluid flow channel in response to said piston being retracted within said barrel portion toward said one end thereof upon liquid having been drawn into said barrel portion and said plug member moved to said forward position by the ejection of at least a portion of said liquid from said barrel portion thereby preventing any additional liquid from being drawn into said barrel portion and rendering said syringe non-reusable.

22. The syringe of claim 21 wherein said plug member comprises a body portion, a cylindrical portion disposed rearwardly of said body portion and defining a rear plug surface at the rearward end thereof, and an annular resilient flange disposed forwardly of said body portion, said flange defining a forward plug surface at the forward end thereof, said retaining means comprising said annular resilient flange, and said fluid flow channel comprising a first fluid passageway disposed in said rearward plug surface and a second fluid passageway disposed in said forward plug surface, said second fluid passageway communicating with said first fluid passageway when said plug member is in said rearward position.

23. The syringe of claim 21 wherein said retaining means comprises a resilient annular flange defined by said plug member, said walled chamber defines a first annular wall portion extending about a rearward portion of said chamber and a second wall portion extending about a forward portion of said chamber and defining an enlarged diameter portion of said chamber, and said closing means comprises an annular shoulder disposed in said chamber between said first and second wall portions, said resilient flange being disposed in a flexed disposition and bearing against said first wall portion of said chamber when said plug member is in said rearward position, extending radially outwardly from said plug member in an unflexed disposition within said enlarged diameter portion of said chamber when said plug member is in said forward position and, upon said piston being retracted within said barrel portion toward said one end thereof when said plug member is in said forward position said flange bears against said shoulder, closing said fluid flow channel.

24. The syringe of claim 21 wherein said walled chamber defines a first annular wall portion extending about a rearward portion of said chamber and a second annular wall portion extending about a forward portion of said chamber and defining an enlarged diameter portion of said chamber, said retaining means comprising an annular resilient flange, said flange defining a forward plug surface at the forward end thereof and annular side wall adjacent thereto, said fluid flow channel extending through said forward plug surface and a forward portion of said adjacent side wall, said flange being disposed in a flexed disposition when said plug member is in a said rearward position with said plug surface bearing against said first wall portion and, upon said plug member being moved to said second position, said flange extends radially outwardly from said plug member within said enlarged diameter portion of said chamber, and wherein said closing means comprises an annular shoulder disposed within said chamber between said first and second wall portions thereof, said shoulder cooperating with said flange to close said fluid flow channel when said plug member is in said forward position and upon said flange being drawn against said shoulder in response to said retraction of said piston.

25. The syringes of claims 23 or 24 including an annular stop member disposed in said barrel portion between said piston and said plug member, said stop member including an inwardly projecting radial portion for limiting the rearward movement of said plug member in said chamber, an aperture in said radial portion for the passage of fluid therethrough and an annular depending portion defining said first wall portion in said chamber and said shoulder.

26. The syringe of claim 21 wherein said retaining means is integrally formed with said plug member and said fluid flow channel comprises a plurality of fluid flow passageways, said passageways being formed in and spaced equidistantly apart about said resilient retaining means.

27. A single use disposable hypodermic syringe comprising:
a hollow elongated barrel portion;
a piston in sealing engagement with and axially translatable along said barrel portion;
a piston rod secured to said piston and projecting from one end of said barrel portion for use in reciprocating said piston;
a walled chamber disposed proximate the other end of said barrel portion, said chamber having a first annular side wall portion extending about a rearward portion thereof, a second annular side wall portion extending about a forward portion thereof and defining an enlarged diameter portion of said chamber, and an annular shoulder disposed in said chamber between said first and second wall portions;
a plug member disposed in said chamber and movable therein from a rearward position to a forward position in response to liquid being forced against said plug member by said piston, said plug member defining a body portion, a cylindrical portion disposed rearwardly of said body portion, and a rear plug surface at the rearward end thereof;
a resilient flange defined by said plug member and disposed thereon forwardly of said body portion, said flange defining a forward plug surface at the forward end thereof, an annular side wall adjacent said forward plug surface, and a diameter greater than the inner diameter of said first wall portion of said chamber and less than the diameter of said second wall portion, said flange being in a flexed disposition and bearing against said first wall portion of said chamber when said plug member is in said rearward position;
a firs fluid flow channel disposed in said flange and extending through said forward plug surface and a forward portion of said annular side wall, said fluid flow channel communicating with said barrel portion, thereby allowing for the passage of fluid therethrough to and from said barrel portion, said flange maintaining said plug member in said rearward position prior to liquid being drawn into said barrel portion and allowing a variable volume of air to be drawn into and ejected from said barrel portion through said fluid flow-channel when said piston is reciprocated within said barrel portion during the use of said syringe as an air pump; and
upon said plug member being moved to said forward position by liquid being forced against such said plug member by said piston, said flange flexes outwardly within said enlarged diameter portion of said chamber such that upon said piston being subsequently retracted within said barrel portion toward said one end thereof, said flange is drawn against said shoulder in said chamber, sealing said fluid flow channel and preventing any additional liquid from being drawn into said barrel portion, thereby rendering said syringe non-reusable.

28. The syringe of claim 27 wherein said cylindrical portion of said plug member defines an annular side wall adjacent said rear plug surface and a second fluid flow channel extending through said rearward plug surface and a forward portion of said adjacent side wall, said second fluid flow channel communicating said first fluid flow channel when said plug member is disposed in said rearward position.

29. A single use disposable hypodermic syringe comprising:
a hollow elongated barrel portion;
a piston in sealing engagement with and axially translatable along said barrel portion;
a piston rod secured to said piston and projecting from one end of said barrel portion for use in reciprocating said piston;
a walled chamber disposed proximate the other end of said barrel portion and defining an annular shoulder therein;
a plug member disposed in said chamber and movable therein from a rearward position to a forward position in response to liquid being forced against said plug member by said piston, said plug member having a fluid flow channel therein for the passage of fluid therethrough to and from said barrel portion when said plug member is in said rearward position and defining a resilient retaining means for retaining said plug member in said rearward position prior to liquid being drawn into said barrel portion and allowing a variable volume of air to be drawn into and ejected from said barrel portion through said channel when said piston is reciprocated within said barrel portion during the use of said syringe as an air pump and, upon liquid being drawn into said barrel portion through fluid flow channel and at least a portion thereof ejected from said barrel portion, said plug member cooperates with said shoulder to seal said channel in response to said piston being retracted within said barrel portion toward said one end thereof, thereby preventing any additional liquid from being drawn into said barrel portion through said channel and rendering said syringe non-reusable.

30. The syringe of claim 29 wherein said fluid flow channel comprises a plurality of fluid flow passageways, said passageways being formed in and spaced equidistantly apart about said resilient retaining means.

31. A single use disposable hypodermic syringe comprising:
a hollow elongated barrel portion;
a piston in sealing engagement with and axially translatable along said barrel portion;
a piston rod secured to said piston and projecting from one end of said barrel portion for use in reciprocating said piston;
a walled chamber disposed proximate the other end of said barrel portion;
a first plug member disposed in said chamber and movable therein from a rearward position to a forward position in response to liquid being forced against said plug member by said piston;
a fluid flow channel extending axially through said first plug member for allowing a variable volume of air to pass therethrough and be drawn into and ejected from said barrel portion when said first plug member is in said rearward position;

means for retaining said first plug member in said rearward position when said piston is reciprocated within said barrel portion prior to liquid being drawn into said barrel portion during the use of the syringe as an air pump;

means for permanently maintaining said first plug member in said forward position upon said plug member being moved to said forward position by liquid being forced against said first plug member by said piston during the ejection thereof from said barrel portion; and a second plug member disposed in said barrel portion forwardly of said first plug member, said second plug member being axially movable within said barrel portion and defining closure means thereon for sealing said fluid flow channel upon said first plug member being disposed in said forward position and said closure means being drawn into sealing engagement with said first plug member by the retraction of said piston within said barrel portion toward said one end thereof.

32. A single use disposable hypodermic syringe comprising:

an elongated barrel portion;

a piston in sealing engagement with and axially translatable along said barrel portion;

a piston rod secured to said piston and projecting from one end of said barrel portion for use in reciprocating said piston;

a walled chamber disposed proximate the other end of said barrel portion, said chamber having a first annular wall portion extending about a rearward portion thereof, a second wall portion extending about a forward portion thereof and defining an enlarged diameter portion of said chamber, and an annular shoulder disposed in said chamber between said first and second wall portions;

a fluid flow channel disposed in said first wall portion and said shoulder communicating said forward portion of said chamber with said rearward portion thereof;

a plug member disposed in said chamber and movable therein from a rearward position to a forward position in response to liquid being forced against said plug member by said piston; and an annular resilient flange carried by said plug member and bearing against said first wall portion of said chamber when said plug member is in said rearward position, retaining said plug member in said rearward position prior to liquid being drawn into said barrel portion and allowing a variable volume of air to be drawn into and ejected from said barrel portion through said fluid flow channel when said piston is reciprocated within said barrel portion during the use of said syringe as an air pump, said flange extending radially outwardly from said plug member within said enlarged diameter portion of said chamber when said plug member is in said forward position and, upon said piston being retracted within said barrel portion toward said one end thereof when said plug member is in said forward position, said flange bears against said shoulder, closing said fluid flow channel and preventing any additional liquid from being drawn into said syringe barrel portion.

33. The syringe of claim 32 wherein said piston rod defines an enlarged portion at the forward end thereof, said portion being received and held within a correspondingly configured recess in said piston such that upon said plug member being disposed in said forward position of said barrel portion and said piston being retracted within said barrel, a vacuum is created between said piston and said plug member causing said enlarged portion of said piston rod to be pulled from said recess, rendering said piston rod incapable of further reciprocating of said piston.

34. The syringe of claim 32 wherein said fluid flow channel comprises a plurality of fluid flow passageways, said passageways extending through and being spaced equidistantly apart about said shoulder and said first wall portion.

35. A single use disposable hypodermic syringe comprising:

an elongated barrel portion;

a piston in sealing engagement with and axially translatable along said barrel portion;

a piston rod secured to said piston and projecting from one end of said barrel portion for use in reciprocating said piston;

a walled chamber disposed proximate the other end of said barrel portion and defining an annular shoulder therein;

a plug member having a rearward end and a forward end and disposed in said chamber proximate said annular shoulder and movable therein from a rearward position to a forward position in response to liquid being forced against said plug member by said piston;

a fluid flow channel disposed in said shoulder and extending rearwardly of said rearward end of said plug member when said plug member is in said rearward position for the passage of fluid therethrough to and from said barrel portion;

a resilient retaining means carried by said plug member for retaining said plug member in said rearward position prior to liquid being drawn into said barrel portion and allowing a variable volume of air to be drawn into and ejected from said barrel portion through said fluid flow channel when said piston is reciprocated within said barrel during the use of the syringe as an air pump and, upon liquid being drawn into said barrel portion through said fluid flow channel and at least a portion thereof ejected from said barrel portion, said resilient retaining means flexes outwardly to cooperate with said annular shoulder to seal said fluid flow channel in response to said piston being retracted within said barrel portion toward said one end thereof, thereby preventing any additional liquid from being drawn into said barrel portion through said channel and rendering said syringe non-reusable.

36. The syringe of claim 35 wherein said retaining means comprises a resilient annular flange defined by said plug member, said walled chamber has a first annular wall portion extending about a rearward portion thereof and a second wall portion extending about a forward portion thereof, said shoulder being disposed between said first and second wall portions, said resilient flange being disposed in a flexed disposition and bearing against said first wall portion in said chamber when said plug members in said rearward position, extending radially outwardly from said plug member in an unflexed disposition within said enlarged diameter portion of said chamber when said plug member is in said second forward position and, upon said piston being retracted within said barrel portion toward said one end thereof when said plug member is in said forward position, said flange bears against said shoulder, sealing said fluid flow channel.

37. The syringe of claim 35 wherein said piston rod defines an enlarged portion at the forward end thereof, said portion being received and held within a correspondingly configured recess in said piston such that upon said plug member being disposed in said forward position of said barrel portion and said piston being retracted within said barrel, a vacuum is created between said piston and said plug member causing said enlarged portion of said piston rod to be pulled from said recess, rendering said piston rod incapable of further reciprocation of said piston.

38. The syringe of claim 35 wherein said fluid flow channel comprises a plurality of fluid flow passageways, said passageways extending through and being spaced equidistantly apart about said shoulder.

* * * * *